United States Patent [19]

Fezzi et al.

[11] Patent Number: 5,068,108
[45] Date of Patent: Nov. 26, 1991

[54] CONTROLLED RELEASE PROTECTIVE MATRICES FOR ZOOTECHNICAL AND VETERINARY USE

[75] Inventors: Luigi Fezzi; Giacomo Grassigli, both of Modena, Italy

[73] Assignee: Industria Italiana Integratori Trei S.P.A., Modena, Italy

[21] Appl. No.: 485,997

[22] Filed: Feb. 27, 1990

[30] Foreign Application Priority Data

Mar. 3, 1989 [IT] Italy ................................ 19639 A/89

[51] Int. Cl.$^5$ ...................... A01N 25/08; A23K 1/18; A61K 9/62; A61K 47/36
[52] U.S. Cl. ................................... 424/438; 424/409; 424/420; 424/425; 424/484; 514/782
[58] Field of Search ............... 424/409, 420, 425, 438, 424/484; 514/782

[56] References Cited

U.S. PATENT DOCUMENTS

| | | | |
|---|---|---|---|
| 3,794,732 | 2/1974 | Raun | 514/460 |
| 3,937,836 | 2/1976 | Raun | 514/460 |
| 3,959,493 | 5/1976 | Boelsrud et al. | 424/438 |
| 4,196,187 | 4/1980 | Dannelly et al. | 424/489 |
| 4,333,919 | 6/1982 | Kleber et al. | 424/438 |
| 4,642,317 | 2/1987 | Palmquist | 514/558 |
| 4,649,042 | 3/1987 | Davis et al. | 424/430 |
| 4,837,004 | 6/1989 | Wu et al. | 424/438 |

FOREIGN PATENT DOCUMENTS 0037478 10/1981 European Pat. Off. .
2132027 11/1972 France .

OTHER PUBLICATIONS

Chem Absts, vol. III, No. 14, Abst. No. 120795v.

*Primary Examiner*—Thurman K. Page
*Assistant Examiner*—Carlos Azpuru
*Attorney, Agent, or Firm*—Walter H. Schneider

[57] ABSTRACT

This invention concerns compositions for zootechnical and veterinary use, characterized in that biologically active substances are incorporated in protective matrices, which have the following properties: 1) controlled release (ruminal by-pass) effect; 2) chemical-physical protection of active principles against degradation induced by technological processes of production, storage and pellettization of fodders for all animal species. The matrices of the invention are characterized by a plastic rheological behaviour due to the presence of lipogelling agents. The obtained products show the following advantages: increased active principle stability in feeds for all animal species; protection of the active principles from attack of Rumen microorganisms in fodder from attack of for ruminants.

2 Claims, No Drawings

CONTROLLED RELEASE PROTECTIVE MATRICES FOR ZOOTECHNICAL AND VETERINARY USE

The present invention relates to compositions for zootechnical and veterinary use with ruminal by-pass effect and/or suitable to preserve biologically active principles, from the chemical-physical degradation occuring in feed, to protective matrices employed in said compositions and to a process for the preparation thereof.

In every field of the industrial zootechnical stock farming, completion of alimentary diet with some biologically active principles is needed, said principles being suitable to cover possible metabolic deficiencies or to increase productive efficiencies, as well as treatment for preventive or therapeutic purpose with different kinds of drugs (antibiotics, chemotherapeutic drugs etc.).

Substances used for alimentary completion and for therapeutic purpose may undergo a loss of titre, more or less notable, depending on the nature thereof, due to technological processes of production, storage and pelletization of feed. This results in a lack of agreement between the expected dose and the actually administered dose of active principles.

In polygastric animals an amount of active principles orally administered is in its turn consumed by Rumen microorganisms and this involves the consequent problems: (1) remarkable degradation of active principles such as vitamins, amino acids and proteins with a consequent drastic decrease in systemic supply; (2) antibacterial action of the administered drugs against ruminal microorganisms making ineffective the oral therapy in ruminants.

In short, an optimal zootechnical or veterinary composition should: for all animal species: grant titre stability of the active principles contained therein, even if subjected to a drastic treatment such as pelletization; for ruminants: enable a rumen by-pass effect, in order to provide suitable systemic supply of the administered active principles and enable antibiotic treatments by the oral route.

The problems cited above are not satisfactorily overcome by the actually available zootechnical compositions.

The use of alkaline earth soaps as fatty carriers in ruminants is known. Indeed, calcium by-passes rumen (by-pass effect) and releases in abomasum the fatty acid which can be used in metabolism.

EP-A 0037478 discloses compositions for administering active principles containing a sodium, potassium or calcium soap combined with long-chain fatty acids and/or hydrogenated fats.

Ruminal protection systems have been developed with long chain fatty acids, but said systems besides not granting a complete by-pass effect, markedly degrade some of the utilized active principles.

It has now been found that protective matrices consisting of substances of lipidic origin, which are lipogelled by addition of suitable substances selected from cellulose derivatives, polyesters, polyalcohols, zinc, manganese, cobalt, aluminium or iron hydroxides, liposoluble or lipo-dispersible polymers, and/or optionally transformed in pastes by addition of substances such as starch, Kaolin, bentonite, silica or other lyophobic or lyophilic colloids.

Said substances of lipidic origin comprise fatty acids, esters thereof, fatty alcohols; mono-, di- and triglycerides and mixtures thereof, selected according to the chemico-physical characteristics of the active ingredients to be protected.

The matrices and compositions formign the objects of the present invention can improve stability of the active principles therein, due to the chemical-physical properties thereof, with the following advantages:

(a) Low heat transmissivity with consequential decrease of incidence of the thermochemical degradation of the active principles held in the matrix.

(b) Decreased permeability to light and therefore decreased photolysis.

(c) Remarkably decreased oxidative processes of the active principles which are protected from direct air-oxygen contact due to the protective film thereover.

(d) High resistance to hydrolytic reactions of active principles given by the hydrophobic nature of the matrix.

(e) Disappearance of interactions between various active principles and between these and the substrate.

(f) Increased resistance to pelletization.

Ruminal by-pass effect is obtained due to the following matrix characteristics:

(1) presence in the interior of the matrix of a tridimensional network substance which, incorporating the active principle, avoids ruminal microorganisms attack.

(2) high melting point of the preparation.

In reticulum and abomasum these materials do not undergo peculiar transformations.

Once in the abomasum, the matrices undergo a first degradation due to the high acidity present, which splits molecules from the gelling agent causing a decreased consistency and an increased porosity of the material.

The so transformed material reaches duodenum where it is emulsified by bile acids and therefore completely releases the active principles contained therein, which are absorbed in the following segments of intestine.

The use in the ruminant feed field of active principles protected by the matrices forming the objects of the present invention shows the following advantages:

(a) increased systemic supply of biologically active principles introduced by diet;

(b) disappearance of negative phenomena against rumen microorganisms, due to oral administration of antibiotic or chemotherapeutic drugs.

The compositions according to the present invention are obtained by a process consisting of the following steps:

step 1: melting lipidic material and mixing the mass;
step 2: adding solutions of lipogelling agents and/or lyophobic or lyophilic colloids;
step 3: controlling chemical-physical parameters and adding the active principles;
step 4: drying under ordinary or reduced pressure the so obtained material.

Lipogelling agent to total mass ratio may range widely, generally from 1 to 90% by weight. Nevertheless, a weight ratio from 2 to 80%, more preferably from 5 to 50%, is preferred to obtain better rheological characteristics.

Under these conditions a matrix is obtained, which is notably desired for the foreseen uses.

Examples of lipogelling agents suitably utilized according to the present invention are either polymeric materials such as ethyl cellulose methyl cellulose, cellulose acetophthalate, polyacrylates, polyvinyl alcohol, polyoxyethylene alcohol or metal hydroxides selected from zinc, aluminium, iron, cobalt and manganese hydroxides. Examples of colloids include bentonite, Kaolin, silica, starch.

As lipidic organic material, fatty acids or esters thereof, mono, di and triglicerides, corresponding alcohols and mixtures thereof, can be used.

The active principles, which can be included in the matrices of the invention, are those commonly used in zootechnics or veterinary practice, for instance B group vitamins, liposoluble vitamins (A, D, E), choline, amino acids, proteins, antibiotics (for instance tetracycline, erithromycine, β-lactams etc.), chemotherapeutic drugs.

The amount of active principles in the compositions will be obviously defined by the kind of the active principle itself or by the intended purpose and it will be easily determined by those skilled in the art.

The compositions forming the object of the invention can obviously contain other excipietns or additives, such as flavours, antioxidants, fillers etc., which will be used according to the conventional modalities.

The following examples are given for illustrative purposes.

EXAMPLE 1

Formulation for zootechnical use of vitamin A and E.

| Vitamin A | I.U. | 50.000.000 |
|---|---|---|
| Vitamin E | g. | 50 |
| Saturated triglycerides | g. | 800 |
| Glycerylmonolaurate | g. | 80 |
| B.H.T. | g. | 2 |
| Ethyl cellulose | g. | 5 |
| Dibutylphthalate | g. | 5 |
| Silica | g. | 5 |
| Flavours | g. | 2 |

EXAMPLE 2

Formulation for zootechnical use of vitamins A, D3, E.

| Vitamin A | I.U. | 100.000.000 |
|---|---|---|
| Vitamin D3 | I.U. | 8.000.000 |
| Vitamin E | g. | 30 |
| Saturated triglycerides | g. | 650 |
| Glycerylmonolaurate | g. | 100 |
| B.H.T. | g. | 2 |
| Maize starch | g. | 90 |
| Bentonite | g. | 100 |
| Flavours | g. | 2 |

EXAMPLE 3

Formulation for zootechnical use of vitamins of group B.

| Vitamin B1 | g. | 30 |
|---|---|---|
| Vitamin B2 | g. | 30 |
| Vitamin B6 | g. | 15 |
| Vitamin B12 | g. | 0.1 |
| Saturated triglycerides | g. | 740 |
| Glyceryl dioleate | g. | 40 |
| Glyceryl monoleate | g. | 40 |
| Bentonite | g. | 100 |
| Cellulose acetophthalate | g. | 2 |
| Ethoxyquine | g. | 2 |
| Flavours | g. | 2 |

EXAMPLE 4

Formulation for zootechnical use of choline.

| Choline chloride | g. | 300 |
|---|---|---|
| Silica | g. | 200 |
| Gliceryl oleate | g. | 200 |
| Polyoxyethylene alcohol | g. | 5 |
| Saturated triglycerides | g. | 295 |

EXAMPLE 5

Formulation for zootechnical use of oxitetracycline.

| Oxytetracycline base | g. | 100 |
|---|---|---|
| Saturated triglycerides | g. | 880 |
| Ethyl cellulose | g. | 5 |
| Cellulose acetophthalate | g. | 5 |
| Methyl cellulose | g. | 0.5 |

EXAMPLE 6

Formulation for zootechnical use of a sulphamidic.

| Sulfamethazine | g. | 100 |
|---|---|---|
| Sulfamerazine | g. | 100 |
| Saturated triglycerides | g. | 740 |
| Glyceryl monolaurate | g. | 50 |
| Tween | g. | 2 |
| Polyacrylates | g. | 5 |

We claim:

1. A rumen by-pass product for oral administration to a ruminant comprising a biologically active component supported by a protective matrix formed by lipogelling a saturated long chain fatty acid triglyceride with a polymeric material selected from methyl- and ethyl cellulose, cellulose acetophthalate, polyvinyl and polyoxyethylene alcohol and polyacrylates, and transforming the matrix into a paste by the addition thereto of a colloidal material selected from starch, kaolin, bentonite and silica.

2. A rumen by-pass product according to claim 1 in which the polymeric material is present in an amount of 5–50% by weight based on the total weight of said product.

* * * * *